United States Patent [19]

Atwood

[11] Patent Number: 4,496,744
[45] Date of Patent: Jan. 29, 1985

[54] MULTIDENTATE MACROMOLECULAR COMPLEX SALT CLATHRATES

[75] Inventor: Jerry L. Atwood, Tuscaloosa, Ala.

[73] Assignee: University of Alabama, University, Ala.

[21] Appl. No.: 125,500

[22] Filed: Feb. 28, 1980

[51] Int. Cl.$^3$ .................................................. C07F 5/06
[52] U.S. Cl. ..................................... 549/208; 549/207
[58] Field of Search ............................. 260/338, 340.3; 549/208, 207

[56] References Cited

U.S. PATENT DOCUMENTS 3,280,025  10/1966  Poe et al. ............................ 208/322
4,024,170  5/1977  Atwood ...................... 260/438.5 R

OTHER PUBLICATIONS

James J. Christensen et al., Chemical Reviews (1974), vol. 74, No. 3, pp. 351–384.

Primary Examiner—Norma S. Milestone
Attorney, Agent, or Firm—Oblon, Fisher, Spivak, McClelland & Maier

[57] ABSTRACT

A liquid clathrate of a multidentate macromolecular compound complex salt of the formula:

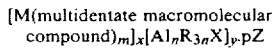

wherein M is a mono-, di, or trivalent cation, R is a lower alkyl group of 1 to 8 carbon atoms, X is a monovalent, divalent or trivalent anion, n is an integer of 2 to 4, x and y are integers from 1 to 3 and m is 1 to 2, Z is an aromatic hydrocarbon compound and p is an integer from 1 to 40. The present liquid clathrate is useful in separating an aromatic hydrocarbon compound from a non-aromatic hydrocarbon compound as well as from a different aromatic hydrocarbon compound.

11 Claims, No Drawings

MULTIDENTATE MACROMOLECULAR COMPLEX SALT CLATHRATES

BACKGROUND OF THE INVENTION

1. Field of the Invention

The present invention relates to clathrates of certain aromatic hydrocarbons and complex aluminum salts. More particularly, the present invention relates to liquid clathrates of aromatic hydrocarbons and complex aluminum salts which contain at least one multidentate macrocyclic compound complexed with the cationic portion of the complex salt.

2. Description of the Prior Art

Liquid clathrates of small ring aromatic compounds and complex metal salts formed by the reaction of simple alkali metal or ammonium salts with trimethylaluminum in a mole ratio of 1:2 are known as described in a series of publications authored by J. L. Atwood et al, in the Journal of Organometallic Chemistry (Vol. 66, pp. 15-21 (1974); Vol. 42, pp. C77-79 (1972); Vol. 61, pp. 43-48 (1973); and Vol. 65, pp. 145-154 (1974). The complex metal salts which form the liquid clathrates with certain aromatic solvents are prepared by reacting simple salts such as the alkali metal or ammonium halides, azides, thiocyanates and selenocyanates with trimethylaluminum in appropriate amounts such that salts of the stoichiometry, $M[Al_2(CH_3)_6X]$ are formed. When the complex metal salts are treated with certain aromatic compounds such as benzene or toluene, liquid complexes or clathrates form which contain at least two and up to about 13 aromatic molecules per complex salt molecule. The liquid clathrates can be distinguished from the rest of the particular aromatic hydrocarbon solvent to which the complex metal salt is exposed by the formation of a second liquid layer which is immiscible with the hydrocarbon solvent.

Liquid clathrates are also known as described in U.S. Pat. No. 4,024,170 which are formed by the complexation of 1.5 to 30 moles of an aromatic hydrocarbon compound and a complex aluminum nitrate salt of the formula $M\{Al_2[(CH_2)_xCH_3]_6NO_3\}$ wherein x is an integer of 1 to 3 and M is an alkali metal cation, ammonium ion, or the like. It is believed that the clathrate forming ability of the aluminum containing salts is attributable to the angular characteristics of the nitrate-containing anion portion of the salt.

U.S. Pat. No. 3,280,025 shows a method of extracting aromatic hydrocarbons from liquid hydrocarbon material by contacting the liquid hydrocarbon material with a complex of a trialkylaluminum and a salt having the formula $R_nMX$, wherein R is alkyl, usually of 2 to 5 carbon atoms, M is one of the elements: nitrogen, arsenic, phosphorous, sulfur, selenium or tellurium, X is a halogen and n is 3 or 4 depending upon the element M. The trialkylaluminum compound and $R_nMX$ compound react to form a complex which selectively forms a clathrate with aromatic hydrocarbons in a liquid hydrocarbon.

While the prior art complex salts all form liquid clathrates with aromatic hydrocarbons, the types of complexes which form clathrates are limited, and the extent of clathrate formation is also limited. A need, therefore, continues to exist for a greater array of complex salts which form clathrates of specific compositions involving a large number of aromatic hydrocarbon molecules per complex salt molecule thereby providing a broader spectrum of choices for a given separation process.

SUMMARY OF THE INVENTION

Accordingly, one object of the present invention is to provide multidentate macrocyclic compound containing complex salts.

Another object of the invention is to provide liquid clathrates of discrete compositions involving an aromatic hydrocarbon and a complex salt whose cationic portion contains a multidentate macrocyclic compound.

Yet another object of the present invention is to provide a method of forming multidentate macrocyclic compound containing complex salts.

Briefly, these objects and other objects of the present invention as hereinafter will become readily apparent can be attained by a multidentate macrocyclic compound complex salt clathrate of the formula:

$[M(\text{multidentate macrocyclic compound})_m]Al_nR_{3n}X_y]_p\cdot pZ$ wherein M is a monovalent divalent or trivalent cation, R is a lower alkyl group of 1 to 8 carbon atoms, X is a monovalent, divalent or trivalent anion, n is an integer of 2 to 4, x and y are integers from 1 to 3, m is 1 or 2, Z is an aromatic hydrocarbon compound and p is an integer of from 1 to 40.

DETAILED DESCRIPTION OF THE PREFERRED EMBODIMENTS

The aluminum containing complex salts which are the basic ingredient of the multidentate macrocyclic compound complexes of the present invention have the following formula:

$M_x(Al_nR_{3n}X)_y$ wherein R is a lower alkyl radical of 1 to 8 carbon atoms, particularly the likes of methyl, ethyl, propyl and butyl; X is a monovalent, divalent or trivalent anion, M is a monovalent divalent or trivalent cation, n is a value of 2 to 4 and x and y vary from 1 to 3 depending upon the valence state of the anion and cation. Suitable types of cationic species $M^{\oplus}$ which form the complex salts include all those which complex with a multidentate macromolecule and include the alkali metals, the alkaline earth metals, quaternary ammonium ions, quaternary arsonium ions, quaternary sulfonium ions, quaternary telluronium ions and mixtures thereof. Specific examples of cationic species include $K^+$, $Rb^+$, $Na^+$, $Cs^+$, $Ca^{+2}$, $Ba^{+2}$, $Sr^{+2}$, $CO^{+2}$, $Ag^+$, $Hg^+$, $Hg^{+2}$, $Pb^{+2}$, $Tl^+$, $Ce^{+3}$, $La^{+3}$, $La^{+3}$, $Cd^{+2}$, $Cr^{+3}$, $Fe^{+3}$, $Mo^{+3}$, $NR'_4^{\oplus}$, $PR'_4^{\oplus}$, $TlR'_2^{\oplus}$, wherein R' is hydrogen, alkyl of $C_1$–$C_{10}$, phenyl or naphthyl and the like, particularly dialkylthallium ions. Suitable monovalent cations also include metals having a normal valence state greater than one such as the alkaline earth metals, and the transition metals such as chromium, iron, cobalt, molybdenum and the like which are covalently bonded to at least one other substituent such as an aromatic hydrocarbon radical or molecule including the likes of phenyl, naphthyl and the like or benzene, toluene and the like such that the net positive charge on the metal-radical entity is one. Examples of radical modified metal species include phenylmercury$^{\oplus}$, dibenzenechromium$^{\oplus}$, dicyclopentadienylcobalt$^{\oplus}$ and the like.

Suitable examples of monovalent, divalent and trivalent anionic species include the likes of the halides, particularly $Cl^-$, $F^-$, $Br^-$, $I^-$, azide, $SCN^-$, $SeCN^-$, nitrite, nitrate, loweralkylacyl such as $CH_3CO_2^-$ and $HCO_2^-$, hydroxide, carbonate, bicarbonate, sulfate and phosphate.

Suitable multidentate macromolecular compounds which can be reacted with cationic species M to form complex cationic species include many types of compounds such as macrocyclic polyethers, macrocyclic polyamines, macrocyclic polythioethers and mixed donor macrocycles. These types of compounds are well known in the art as described by Christensen et al. in *Chemical Reviews*, 74(3), pp. 351+. The complex cationic species is formed by coordination of most or all of the available coordination sites in cation M with the donor atoms of the given multidentate macromolecule employed.

A preferred class of complex cationic species within the scope of the present invention includes those species formed by the interaction of a cation M of the above complex salt with one or two macrocyclic polyether or crown ether molecules. The crown ether-complex salt complex has the formula: $[M(crown\ ether)_m]_x$-$[Al_nR_{3n}X]_y$, wherein M, R, X, n, x and y are as defined above and m is 1 or 2. Suitable crown ethers useful in forming a crown ether complex include those of the formula:

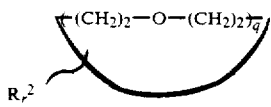

wherein q is 4–8 and $R^2$ is a lower alkyl, aryl or aryl which is fused to said ring, and r is an integer of 0–4. Specific examples of crown ethers include 18-crown-6, 15-crown-5, dibenzo-18-crown-6, 21-crown-7, dicyclohexyl-18-crown-6, benzo-15-crown-5, benzo-12-crown-4, dibenzo24-crown-8, dibenzo-30-crown-10 and the like. 18-Crown-6 and dibenzo18-crown-6 are especially good coordinating agents for potassium ions. Sodium is generally best bound by 15-crown-5. The binding is directly related to the size of the cavity which in turn is related to the size of the crown for crown ethers, i.e. the larger the cation, the larger the crown needed.

In the formation of the crown ether-cation M complex one or more crown ether molecules may complex with a single M cation species as follows:

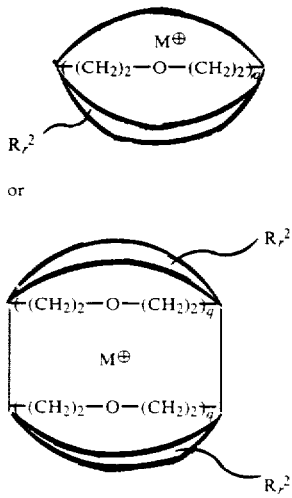

In addition to being one of the variety of monovalent cations described above, cation $M^\oplus$ may also be a crown ether complex of one of the divalent metals or trivalent metals elucidated above.

The liquid clathrates of the present invention are formed by the interaction between a multitude of aromatic hydrocarbon molecules and a single multidentate macromolecular compound containing salt complex and can be represented by the formula:

[M(multidentate macromolecular compound)$_m$]$_x$(Al$_n$R$_{3n}$X)$_y$·pZ.

wherein M, R, X, n, m, x and y are as defined above, p is a value ranging from 1 to 40 and Z is an aromatic hydrocarbon compound. Suitable hydrocarbon aromatic compounds which can be used in forming the clathrate include benzene, toluene, o-, m- or p-xylene, mesitylene, tetramethylbenzene, ethylbenzene, diethylbenzene, cumene, dipropylbenzene, diisopropylbenzene, naphthalene, tetralin, anthracene, or phenanthracene. Benzene and toluene have been demonstrated to give good results. It has been observed that the larger the cation M component of the clathrate, the greater will be the number of molecules of aromatic hydrocarbon compound which can be entrapped in the multidentate macromolecular compound containing complex salt complex.

In general, the anionic component of the complex salt must have the angular geometry

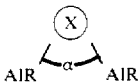

in order to form the aromatic clathrate; whereas a symmetrical anionic structure

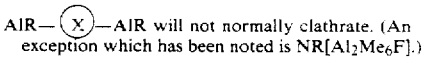

AIR—(X)—AIR will not normally clathrate. (An exception which has been noted is NR[Al$_2$Me$_6$F].)

The nature of the clathrate interaction is thus related to the anion, the lattice energy, the size of the cation and the size of the aromatic molecule.

"Liquid Clathrate" is a term of art which refers to certain enclosure compounds. A liquid clathrate is a loose structure of a complex salt and aromatic compound molecules whereby the aromatic compound is entrapped into layers in the liquid structure. The aromatic compound can be retrieved unchanged by lowering the temperature. The liquid clathrate will only accomodate a certain number of aromatic molecules and the excess aromatic molecules will be immiscible with the clathrate. See J. L. Atwood et al, Journal Organometallic Chemistry 66, 15–21 (1974); 42, C 77–79 (1972); 61, 43–48 (1973); 65, 145–154 (1974).

In order to prepare the complex salt, an alkylaluminum compound can be reacted with a simple salt such as an alkali metal nitrate, carbonate, sulfate, azide or the like. In order to form a multidentate macromolecule containing complex of the complex salt, the macrocyclic compound can simply be added to the complex salt in a one step process. Alternatively, the multidentate macromolecular compound containing complex salt can be formed by simultaneously mixing macrocyclic compound, a simple salt and an alkylaluminum compound in a one step process, by adding an alkylaluminum compound to a solution or suspension of a simple salt in a macrocyclic compound in a two step process or by adding a simple salt to a solution of an alkylaluminum compound in a macrocyclic compound.

The liquid clathrate of the multidentate macrocyclic compound containing complex salt can be formed by any one of a number of single step and multi-step process. Thus, the clathrate can be formed in a one step process by simultaneously mixing a simple salt, an alkylaluminum compound and a macrocyclic compound in an aromatic hydrocarbon solvent. Alternatively, a solution of an alkylaluminum compound in an aromatic hydrocarbon can be combined with a solution or suspension of a simple salt in a macrocyclic compound. (A suspension will work as long as the salt has some slight solubility in the solvent.) The order of addition of clathrate components is not critical and any such combination of the components of the liquid clathrate can be employed to successfully prepare the liquid clathrate of the present invention.

The alkylaluminum compound used in the preparation of the complexes of the present invention is normally a trialkylaluminum compound.

The clathrate complex salt or multidentate macromolecular compound containing complex salt forming reaction can occur at room temperature or higher, up to about 190° C., depending on the particular choice of materials. Beyond 190° C., the aluminum alkyl will decompose. Good results are attainable in the range of 15°–80° C. With respect to the clathrate, upon cooling from elevated temperatures, a temperature will be reached at which the clathrate will decompose back to the complex salt and the aromatic compound. The only important consideration which must be given with respect to any of the synthetic procedures by which the complex salt, multidentate macromolecular compound containing complex salt and liquid clathrate are prepared is that since the alkylaluminum compound is sensitive to air and water, the synthesis reactions should be conducted in the absence of both air (oxygen) and water.

Specific examples of liquid clathrates of crown ether-complex salt complexes include:

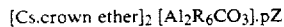

[K.dibenzo-18-crown-6][$Al_2(CH_3)_6N_3$]·$9C_6H_6$

As indicated above, the presence of the crown ether complex within the complex salt has the effect that clathrates of different, but discrete, compositions can be formed in contrast to conventional clathrates. Thus, for example, contrast the conventional clathrate:

K[$Al_2(CH_3)_6NO_3$]·7.0 $C_6H_6$ with the corresponding dibenzo-18-crown-6 containing clathrate of the present invention, which has the following formula:

[K.dibenzo-18-crown-6][$Al_2(CH_3)_6NO_3$]·12.2 $C_6H_6$

Another representative comparison involves the known clathrate:

[Cs][$Al_2(CH_3)_6NO_3$]·12.0 $C_6H_6$, and the corresponding dibenzo18-crown-6 clathrate of the present invention:

[Cs.dibenzo-18-crown-6][$Al_2(CH_3)_6NO_3$]·20.2 $C_6H_6$

The clathrates of the present invention are useful in the separation of an aromatic hydrocarbon compound from non-aromatic hydrocarbon compounds as well as from a different aromatic hydrocarbon compound. For instance, a given multidentate macromolecular compound containing complex salt can be mixed in a solution of benzene and a non-aromatic hydrocarbon such as hexane and the liquid clathrate with benzene will form. The liquid clathrate will separate from the non-aromatic hydrocarbon solution as a separate phase and therefore is easily recovered. The clathrate subsequently can be broken with release of the aromatic hydrocarbon by cooling the clathrate phase or by adding water to the clathrate phase which will destroy the multidentate macromolecular compound containing complex salt.

In another type of separation a mixture of aromatic compounds such as for instance, benzene and toluene can be separated by forming a liquid clathrate of the mixture with a given multidentate macromolecular compound containing complex salt. The liquid clathrate will preferentially form with the molecules of the aromatic hydrocarbon compound which has a greater tendency to form a clathrate with the given macrocyclic compound complex employed. When the clathrate phase is separated from the residual solution and the clathrate is broken, the aromatic hydrocarbon obtained will contain a greater percentage of the aromatic preferentially incorporated in the clathrate. By repeating the separation a sufficient number of times, the original solution can be separated into its individual components.

The multidentate macromolecular compound containing complex salt can also be used to separate an aromatic hydrocarbon dissolved in other non-hydrocarbon, non-active proton containing solvents such as ethers, thioethers, and the like as long as the donor strength of the nonhydrocarbon solvent is not greater than that of the anion X of the complex salt.

Having generally described this invention, a further understanding can be obtained by reference to certain specific examples which are provided herein for purposes of illustration only and are not intended to be limiting unless otherwise specified.

EXAMPLE 1

SEPARATION OF BENZENE ($C_6H_6$) FROM CYCLOHEXANE ($C_6H_{12}$)

A 1.32g (0.005 mole) amount of 18-crown-6 was mixed with 0.40g $KN_3$ (0.005 mole) in a mixture of 3.52g $C_6H_6$(4.00 ml) and 3.12 g $C_6H_{12}$ (4.00 ml). 1ml of $AlMe_3$ (0.010 mole) was added, and the liquid clathrate immediately formed. After 15 minutes an nmr sample was taken from the bottom layer (the liquid clathrate). The complete mass balance was obtained as shown in the table below from the analysis of the nmr spectrum of the liquid clathrate, and confirmed by analysis via an nmr spectrum of the top layer.

|  | Parent* | $C_6H_6$ | $C_6H_{12}$ | Total |
|---|---|---|---|---|
| Charge weight (g) | 2.44 | 3.52 | 3.12 | 9.08 |
| Liquid Clathrate weight (g) | 2.44 | 1.99 | 0.84 | 5.27 |
| Residual charge weight (g) | 0 | 1.53 | 2.28 | 3.81 |

*Parent is [K.18-crown-6] [$Al_2Me_6N_3$]

Separation factor = $\alpha = \frac{1.99/0.84}{1.53/2.28} = 3.53$

The above experiment is completely reproducible. A better $\alpha$ value is obtained by longer residence before nmr analysis. After 3 days essentially pure $C_6H_6$ was found in the liquid clathrate layer. Note, however, at room temperature there is some tendency for the parent compound to crystallize.

EXAMPLE 2

SEPARATION OF BENZENE ) ($C_6H_6$) FROM MESITYLENE, $C_6H_3Me_3$,

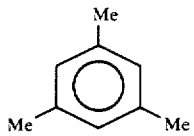

A 1.32g amount of 18-crown-6 (0.005 mole) was mixed with 0.40g (0.005 mole) of $KN_3$ in a mixture of 4.40 $C_6H_6$ (approx. 5 ml.) and 4.30g $C_6H_3Me_3$ (approx. 5 ml). 1 ml (0.010 mole) of $AlMe_3$ was added, and the liquid clathrate formed immediately. After 15 min. an nmr sample was taken from the bottom layer (the liquid clathrate) and the mass balance, obtained as in Example 1, is as follows:

|  | Parent | $C_6H_6$ | $C_6H_3Me_3$ | Total |
|---|---|---|---|---|
| Charge weight (g) | 2.44 | 4.40 | 4.30 | 11.14 |
| Liquid clathrate weight | 2.44 | 2.65 | 2.05 | 7.14 |
| Residual charge weight | 0 | 1.75 | 2.25 | 4.00 |

$$\alpha = \frac{2.65/2.05}{1.75/2.25} = 1.67$$

The experiment is completely reproducible, and $\alpha$ values improve with time, although not as rapidly as in the case of Example 1.

Having now fully described the invention, it will be apparent to one of ordinary skill in the art that many changes and modifications can be made thereto without departing from the spirit or scope of the invention as set forth herein.

What is claimed as new and intended to be secured by Letters Pat. No. is:

1. A liquid chathrate of a crown ether complex salt of the formula:

$$[M(crown\ ether)_m]_x[Al_nR_{3n}X]_y \cdot pZ$$

wherein M is a mono-, di- or trivalent cation, R is a lower alkyl group of 1 to 8 carbon atoms, X is a mono-, di- or trivalent anion, m is 1 or 2, n is 2, 3 or 4, x and y are each an integer of 1 to 3, Z is an aromatic hydrocarbon compound and p is an integer of 1 to 40.

2. The clathrate of claim 1, wherein M is a monovalent cation selected from the group consisting of $Na^+$, $K^+$, $Rb^+$, $Cs^+$, $Ag^+$, $Hg^+$, $Tl^+$, $NR_4'+$ and $TlR_2'+$ wherein R' is hydrogen, phenyl, naphthyl or alkyl of 1 to 10 carbon atoms.

3. The clathrate of claim 1, wherein M is a divalent cation selected from the group consisting of $Ca^{+2}$, $Ba^{+2}$, $Sr^{+2}$, $Hg^{+2}$, $Co^{+2}$, $Pb^{+2}$ and $Cd^{+2}$ or a trivalent cation selected from the group consisting of $Ce^{+3}$, $La^{+3}$, $Cr^{+3}$, $Mo^{+3}$ and $Fe^{+3}$.

4. The clathrate of claim 1, wherein M is a monovalent cation derived from a metal having a normal valence state greater than one but having at least one valence position occupied as a covalent bond with a substituent such that the net positive ionic charge on said metal is one.

5. The clathrate of claim 1, wherein said R group is methyl, ethyl, propyl or butyl.

6. The clathrate of claim 1, wherein X is a halide, azide, $SCN^-$, $SeCN^-$, $NO_3^-$, $NO_2^-$, lower alkylacyl, $OH^-$, $CO_3^=$, $HCO_3^-$, $SO_4^=$ or $PO_4^5$.

7. The clathrate of claim 1, wherein said crown ehter is 18-crown-6, 15-crown-5, dibenzo-18-crown-6, 21-crown-7, dicyclohexyl-18-crown-6, benzo-15-crown-5, benzo-12-crown-4, dibenzo-24-crown-8 or dibenzo-30-crown-10.

8. The chathrate of claim 1, wherein said crown ether has the formula:

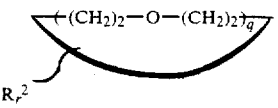

wherein q is 4–8 and $R^2$ is lower alkyl, aryl or aryl fused to said ring and r is 0–4.

9. The clathrate of claim 1, wherein said monovalent cation-crown ether complex has the structure:

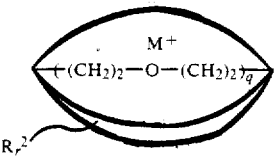

wherein q is 4–8 and $R^2$ is lower alkyl, aryl or aryl fused to said ring and r is 0–4.

10. The clathrate of claim 1, wherein said monovalent cation-crown wherein q is 4–8 and $R^2$ is lower alkyl, aryl or aryl fused to said ring and r is 0–4.

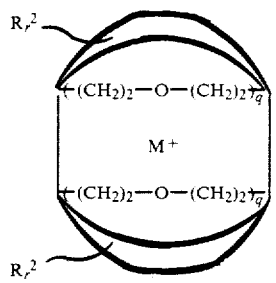

wherein $R^2$, r and q are as defined above.

11. The clathrate of claim 1, wherein said component Z is benzene, toluene, o-, m-, or p-xylene, mesitylene, tetramethylbenzene, ethylbenzene, diethylbenzene, dipropylbenzene, diisopropylbenzene, cumene, naphthalene, tetralin, anthracene, or phenanthracene.

* * * * *